United States Patent [19]

Cross et al.

[11] 3,963,741

[45] June 15, 1976

[54] 4-ALKYL-1,2-DIMETHYL-3,5-DIPHENYLPYRAZOLIUM SALTS AND DERIVATIVES THEREOF AS FUNGICIDAL AGENTS

[75] Inventors: Barrington Cross, Rocky Hill; Bryant Leonidas Walworth, Pennington, both of N.J.

[73] Assignee: American Cyanamid Company, Stamford, Conn.

[22] Filed: Oct. 2, 1975

[21] Appl. No.: 619,092

Related U.S. Application Data

[62] Division of Ser. No. 574,067, May 2, 1975.

[52] U.S. Cl. .................................. 260/311; 424/273
[51] Int. Cl.² .................. C07D 231/12; A01N 9/22
[58] Field of Search .................... 260/311; 424/273; 71/92

[56] References Cited
UNITED STATES PATENTS 3,867,403  2/1975  Feeny ................................... 71/92

3,882,142  5/1975  Walworth et al. .................. 260/311

FOREIGN PATENTS OR APPLICATIONS 825,071  7/1975  Belgium
1,270,379  4/1972  United Kingdom ................. 424/273

OTHER PUBLICATIONS

Elguero et al., Bull. Soc. Chem. 1121 (1970).

*Primary Examiner*—Donald B. Moyer
*Attorney, Agent, or Firm*—Harry H. Kline

[57] ABSTRACT

There are provided novel 4-alkyl-1,2-dimethyl-3,5-diphenylpyrazolium compounds having fungicidal utility. There is also provided a method for both controlling fungi with a fungicidally effective amount of 4-alkyl-1,2-dimethyl-3,5-diphenylpyrazolium salt and protecting living plants from attack by fungi through the application to the foliage of said plants of a fungicidally effective amount of said pyrazolium salt.

9 Claims, No Drawings

4-ALKYL-1,2-DIMETHYL-3,5-DIPHENYL-PYRAZOLIUM SALTS AND DERIVATIVES THEREOF AS FUNGICIDAL AGENTS

This application is a divisional of our co-pending application, Ser. No. 574,067, filed May 2, 1975.

The present invention relates to novel pyrazolium compounds represented by the formula:

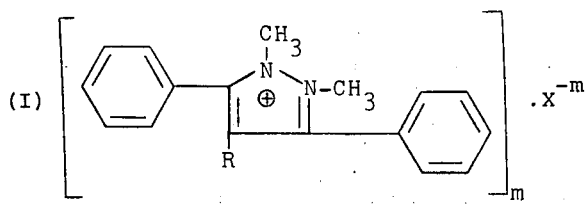

wherein R is a member selected from the group consisting of alkyl $C_2$-$C_5$, allyl, propargyl, benzyl and carbethoxymethyl; X represents an anion with a charge of 1, 2 or 3 and preferably 1; m represents an integer selected from 1, 2 or 3. Still further, the invention relates to a method for controlling pathogenic fungi with a fungicidally effective amount of a Formula (I) pyrazolium compound. This invention further relates to a method for protecting living plants from attack by pathogenic fungi through the application of the foliage of said plants a fungicidally effective amount of a Formula (I) pyrazolium compound.

Illustrative of the anion, represented by X, which is suitable for use in the present invention are, for example, halides such as chloride, bromide or iodide; acetate, hydroxide, sulfate, hydrogen sulfate, methyl sulfate, benzene sulfonate, p-toluene sulfonate, nitrate, phosphate, perchlorate, $I_3^-$, and $Br_3^-$. Further, certain multivalent anions such as sulfate, phosphate, and the like can have associated with them a cation in addition to the pyrazolium compound (I) as, for example, a proton or an alkali metal or alkaline earth metal. For simplicity, such anions are portrayed as being unionized, although they probably are in fact further ionized. Typical representations are: $NaSO_4^-$, $KPO_4^=$, $MgPO_4^-$, $HSO_4^-$, $NaHPO_4^-$, $CaPO_4^-$, and the like.

As is known Elguero et al., in Bull. Soc. Chim. Fr., 1121 (1970), described the compound: 3,5-diphenyl-1,2,4-trimethylpyrazolium iodide. However no utility is disclosed or suggested therein. Further, the U.S. Pat. No. 3,818,096, to Sherlock issued on June 18, 1974, discloses compositions of 1,2-lower dialkyl arylpyrazolium quaternary salts and a method of lowering blood sugar levels with said compounds. In no way does patentee teach or suggest fungicidal activity utilizing any pyrazolium salt; nor does the patentee specifically suggest or contemplate any 4-benzyl, 4-alkynyl or carbethoxymethyl-1,2-dialkyl-3,5-disubstituted pyrazolium salts.

In general pyrazolium salts of the invention are conveniently synthesized by reacting an alkali metal salt of 1,3-diphenyl-1,3-propanedione with an alkylating agent. The thus-obtained substituted propanedione is next reacted with methylhydrazine to yield the appropriately substituted pyrazole. Finally, the thus-obtained pyrazole is quaternized with a methylating agent to yield the desired pyrazolium salt. The above reaction sequence may graphically be illustrated as follows:

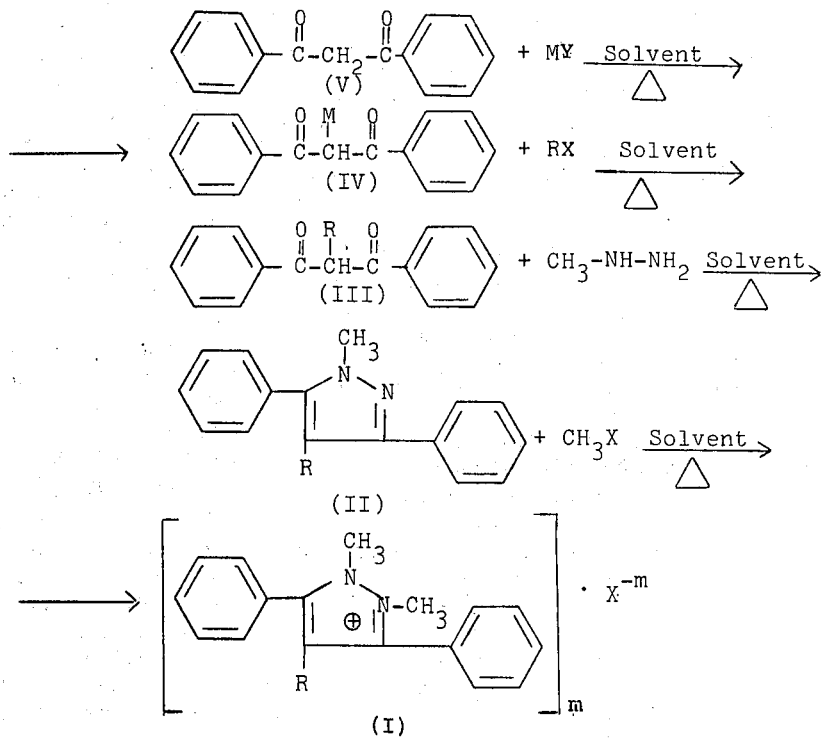

wherein M is an alkali metal such as sodium, potassium, or lithium, and Y is hydrogen, hydroxy, or alkoxy. Exemplary of such compounds are: sodium hydroxide, potassium-t-butoxide, sodium ethoxide, and equivalents of the same.

Advantageously, the alkali metal salt of 1,3-diphenyl-1,3-propanedione can be obtained by reacting an alkali metal hydride, preferably sodium hydride, with said 1,3-diphenyl-1,3-propanedione in the presence of a solvent, such as diethyl ether, methylethyl ether or di-n-propyl ether. This reaction is usually conducted at a relatively low temperature, i.e. at 0° to 20°C. and, preferably, between 5° and 15°C. Thus-formed salt is then reacted with an alkylating reagent, or an alkynylating, carbethoxymethyl alkylating or benzylating reagent. Suitable reagents for this reaction include: alkyl $C_1$–$C_5$, allyl, propargyl, benzyl and carbethoxymethyl halides, preferably the iodides, bromides or chlorides of the above-identified groups.

The reaction is usually carried out at an elevated temperature, generally between about 50° and 150°C. and preferably between 50° and 100°C., in the presence of an anhydrous solvent, such as a dry dialkyl ether as for instance methyl ethyl ether, or a ketone such as acetone, methyl isobutyl ketone, cyclohexanone, dimethylformamide (DMF) or the like. Generally, about 2 to 3 moles of the alkylating reagent per mole of the alkali metal ketonic salt are effective for driving the reaction to completion.

The thus-formed substituted 1,3-diphenyl-1,3-propanedione is then reacted with methylhydrazine. Since the diketone and the methylhydrazine reactant combine in equimolar quantities, it is preferable to maintain the molar ratio of reactants at about 1:1; however a slight excess (up to about 10%) of either reactant may be used. Further, the ring forming reaction between the diketone and methylhydrazine is preferably carried out by combining the aforementioned reactants in an inert solvent therefor and heating to the reaction temperature. Suitable temperatures are in the range of from about 70° to about 150°C. and, preferably, between 80° and 120°C. Suitable solvents include, for example, aprotic solvents, such as xylene, toluene, benzene, pyridine, DMSO and the like, or protic solvents, such as $C_1$–$C_4$ alcohols, preferably n and i-propanol. Where the latter solvents are employed, high rates of conversion are obtained at temperatures in the range of 80° to 85°C.

Quaternization of the 1-methylpyrazole is effected by reaction thereof with at least an equimolar quantity of a methylating agent such as methyl chloride, bromide, iodide; dimethyl sulfate; trimethylphosphate; methyl-p-toluenesulfonate and equivalents of the same.

The latter reaction is preferably conducted in the presence of an inert solvent, such as a lower alcohol $C_1$–$C_4$; a ketone, such as acetone, methyl ethyl ketone, methyl isobutyl ketone or cyclohexanone; an aprotic solvent, such as dimethylsulfoxide or dimethylformamide; or preferably, an aprotic solvent, such as xylene, toluene, benzene or 1,2-dichloroethane. Quaternization is usually carried out at temperatures maintained between 35° and 150°C, preferably between 50° and 125°C.

Since the reactants combine in equimolar quantities in the quaternization reaction, it is preferred to employ a 1:1 molar ratio thereof; however a slight excess (up to 10%) of either reactant may be employed. If the alkylating agent is volatile at the temperatures used, such as is in the case of methyl chloride, it is preferred to conduct the reaction in a sealed pressure vessel.

In carrying out the above ring closure and alkylation reactions, it is expedient to initially form a salt having an anion other than that which it is desired to employ in the fungicidal processes of the present invention. In such cases, the exchange in anion may be conveniently made in a subsequent step. The exchange can be effected by treating the initially formed salt with an ion exchange resin. As a suitable ion exchange resin, one can mention a strong base organic anion exchanger, such as Dowex 1-X8, which is a quaternary alkylammonium resin. Where the resin is supplied as the salt of an anion other than that desired, it is pretreated with an aqueous solution of a salt of the desired anion. For instance, if the resin is supplied as a quaternary ammonium chloride and it is desired to produce a pyrazolium nitrate, one would pretreat the resin with an aqueous solution of sodium nitrate.

Other optional subsequent modifications of the anion in the pyrazolium salt may be effected. For example, a pyrazolium chloride can be conveniently converted to the corresponding bromide or iodide by treatment with sodium bromide or sodium iodide, respectively, in a solvent, such as acetone or water. A pyrazolium salt, such as the chloride may be converted to the corresponding perchlorate by treatment of an aqueous solution of said salt with perchloric acid. This results in the preparation of the less soluble perchlorate salt.

Advantageously, the pyrazolium salts generally demonstrate a high degree of water solubility and lend themselves to the preparation of aqueous concentrates. Among the preferred salts are the methyl sulfates, hydrogen sulfates, iodides and perchlorates. In practice, the aqueous concentrates may be applied directly as a liquid spray to the foliage of plants or they may be further diluted with water and applied as dilute aqueous sprays to said plants.

It has been found that the compounds of this invention are useful for the control of fungi which infect many living plants. They are particularly effective for controlling powdery mildew, especially on grains such as barley and wheat, on vines such as cucumbers, grapes and pumpkin and on fruit and nut trees such as apples, pears and pecans. However, they are also effective for controlling fungi which are the causative agents for rice blast, and apple scab.

In utilizing the above-identified pyrazolium salts for protecting plants from pathogenic fungi, it has been found most advantageous to apply the active material to the foliage of the plant in the form of a liquid, preferably as an aqueous spray. Solutions or suspension containing from about 20 ppm to 5600 ppm and, preferably from 50 to 500 ppm of the pyrazolium cation are generally highly effective for this use.

As the pyrazolium salts disclosed herein exhibit substantial water solubility, such salts can simply be dissolved in water and applied directly, or a surfactant or mixture of surfactants can be added to an aqueous mixture thereof.

The pyrazolium salts of the present invention can also be prepared as wettable powders or as water miscible concentrates which are diluted with water or other suitable polar solvent, generally at the site of use, and then applied as a dilute aqueous spray. Generally, such sprays are applied at the volume rate of from about 938 l/ha to 1877 l/ha or about 100 to 200 gal per acre. It is, of course, obvious that smaller or larger volumes of liquid spray may be employed. For instance, from 400 to 4000 l/ha can be used depending on a plurality of factors such as type of crop, the plant spacing and the amount of foliage per plant being treated.

While fungicides treatments are generally discussed in terms of concentration of active ingredient in ppm in the solution or suspension, it should also be noted that, with the compounds of the present invention, it is generally desirable to apply the pyrazolium salt in an amount sufficient to provide from about 0.56 to 11.8 kg/ha and, preferably, from 0.56 to 4.48 kg/ha of said salt.

Wettable powder formulations can be prepared by grinding together about 25 to 95% by weight of the pyrazolium salt and about 75 to 5% by weight of a solid diluent such as attapulgite, kaolin, bentonite, diatomaceous earth, silica, talc, fullers earth or the like. To this mixture is added about 1 to 5%, by weight, of a dispersing agent, such as the calcium salt of a polymerized alkyl aryl sulfonic acid, sodium lignosulfonate, or sodium salt of condensed naphthalene sulfonic acid and about 1 to 5%, by weight, of a surfactant, such as polyoxyethylated vegetable oil, alkyl phenoxy polyoxyethylene ethanol, sodium alkyl naphthalene sulfonate is also blended with the formulation.

The water-miscible concentrates are prepared by dissolving from 15 to 70% by weight of the compound in 85 to 30% by weight of a water-miscible solvent, such as water itself or another polar water-miscible solvent, such as 2-methoxyethanol, methanol, propylene glycol, diethylene glycol, diethylene glycol monoethyl ether, formamide, and methylformamide. Application of the material is made by adding a predetermined quantity of the water-misolble concentrate to a spray tank and applying as such or in combination with additional suitable diluent, such as a further quantity of water or one of the above polar solvents mentioned above.

The performance of the product in the above formulations, which are applied as liquid sprays, is improved by adding a surfactant or blend of surfactants thereto. Conventional nonionic surfactants are preferred and the surfactants are, preferably, added to the spray tank at the rate of 0.1 to 5%, by volume, to provide good wetting of the spray solution on plant foliage.

Suitable nonionic surfactants include alkyl polyoxyethylene ethers, polyoxyethylene (20) sorbitan monolaurate, polyoxyethylene (20) sorbitan monooleate, alkylanylpolgylool ethers, alkyl phenol ethoxylates, trimethyl nonyl polyethylene glycol ethers, alkyl phenol ethylene oxide condensates, octyl phenoxy polyethoxy ethanols, nonylphenyl polyethylene glycol ethers, condensates of polyoxy ethylenes, polyoxy propylenes, aliphatic polyethers, aliphatic polyesters, alkylaryl polyoxyethylene glycols, and the like. Especially preferred are nonionic surfactants having a hydrophilic-lipophilic balance (HBL) of from 11 to 16. This conventional surfactant classification test is described, for instance, at pages 232 et seq. of *Emulsion Theory and Practice* by Paul Becker, Rheinholt Publishing Corporation, second edition (1965); also available as No. 162 in the American Chemical Society's Monograph Series.

The present invention and preparation of the starting materials therefor as further illustrated by the following examples which are not to be taken as being limited thereto. Unless otherwise stated, all parts and percentages are by weight, in the following illustration and examples as well as in the claims and the discussion above.

EXAMPLE 1

To determine the effectiveness of the 4-substituted 1,2-dimethyl-3,5-diphenylpyrazolium salts as fungicidal agents a variety of pathogenic fungi, host plants and salts are used in the following tests. Pathogens, host plants, the method of testing and the rating system used are reported below along with the data obtained.

Pathogens:

*Piricularia oryzae* Cavara, the rice blast pathogen.
*Venturia inaequalis* (Cke.) Wint. which causes apple scab.
*Erysiphe cichoracearum* DC, the cause of powdery mildew on cucurbits.
*Podosphaera leucotricha* (E. & E.) Salm., the cause of powdery mildew of apples and pears.
*Erysiphe graminis* F. sp. *tritici* the cause of powdery mildew on wheat.
*Erysiphe graminis* f. sp. *hordei* the cause of powdery mildew on barley.

Host Plants

Rice (*Oryza sativa*) Cv. Nato)
Cucumber (*Cucumis sativus*) (Cv. Marketer)
Apple (*Malus sylvestris*) (Seedling)
Wheat (*Triticum aestivum* Cv. Bonanza)
Barley (*Hordeum vulgare* Cv. Larker)

Plants are individually grown in 5.08 cm peat squares and assembled in 7.62 cm × 25.4 cm pressed fibre flats the week prior to spraying. With exception of rice, barley, and wheat, a single specimen of each species is used. A separate flat is used for those plants in the mildew evaluation The complete test system is shown below.

| Series 1 | Series 2 |
|---|---|
| Rice: Rice Blast | Apple: Powdery Mildew |
| Apple: Apple Scab | Cucumber: Powdery Mildew |
|  | Wheat: Powdery Mildew |
|  | Barley: Powdery Mildew |

Spray solutions are prepared at a final concentration of 100 ppm or 500 ppm in 50 ml of 50% aqueous acetone. Acetone is added to solubilize the compound and solutions made to final volume with deionized water.

Two flats with plants for each treatment, one each from Series 1 to 2 (see above), are sprayed simultaneously on a turntable with 50 ml of the test solution. Spray is provided by two fixed Spraying System Company nozzles mounted to deliver vertical and horizontal solid cone spray patterns. Immediately thereafter, all plants are returned to the greenhouse to permit the deposit to dry. After the plants have dried, Series 1 to 2 are separately inoculated. Plants in Series 1 are inoculated with conidial suspensions of the respective pathogens using a Devilbliss paint sprayer operated at air pressure 0.28–0.42 kg/cm$^2$ and immediately transferred to a controlled temperature/humidity cabinet (ambient temperature, RH. 95%). Plants in Series 2 are dusted with respective powdery mildew conidia and then removed to the controlled environment plant culture room (10 hours light, at 22°C, RH. 45%) to await disease development. Plants in Series 1 are held 4 days in the cabinet, then transferred to the greenhouse to await disease expression.

Performance Rating

All plants are rated for disease severity on a scale of 1 to 7 (clean to kill), as described below:

| Rating | Description |
| --- | --- |
| 1 | Clean |
| 2 | Trace disease |
| 3 | Slight disease |
| 4 | Moderate disease |
| 5 | Heavy disease |
| 6 | Severe disease |
| 7 | Kill |

In the accompanying tables of results, the numerical rating is used for clarity.

Data obtained are reported in Tables I and II below. The ratings reported represent data obtained from one or more individual tests. Where more than one test has been conducted the ratings are averaged and reported as a single value rating. For each table, there is also provided a rating value for the checks employed. It is, of course, obvious that the lower the value, the more effective the disease control. When a superscript is used in the table with a rating, it indicates some phytotoxicity. The legends, S means slight, M means moderate, and SV means severe phytotoxicity. Data are reported for minimum effective levels at which compounds are evaluated.

Table I

| Compound | Disease Severity of Plants Sprayed to Run-off with Indicated Rates, ppm | | | | | |
| --- | --- | --- | --- | --- | --- | --- |
| | Rice Blast | | | Apple Scab | | |
| | 500 | 100 | 50 | 500 | 100 | 50 |
| Untreated Controls | | 4.8 | | | 6.0 | |
| 4-Benzyl-1,2-dimethyl-3,5-diphenyl-pyrazolium hydrogen sulfate; | | | | | 5.0 | |
| 4-Benzyl-1,2-dimethyl-3,5-diphenyl-pyrazolium perchlorate; | | | | | 4.0 | |
| 4-(Carboxymethyl)-1,2-dimethyl-3,5-diphenylpyrazolium iodide-, ethyl ester; | 4.0 | | | | SV | |
| 1,2-Dimethyl-3,5-diphenyl-4-ethylpyrazolium methyl sulfate [and hydrogen sulfate(1:1)]; | | | | | 5.0 | |
| 1,2-Dimethyl-3,5-diphenyl-4-n-pentyl-pyrazolium perchlorate; | | | | | 4.0 | |
| 1,2-Dimethyl-3,5-diphenyl-4-n-propyl-pyrazolium perchlorate; | | | | | 5.0 | 4.5 | 5.0 |
| 1,2-Dimethyl-3,5-diphenyl-4-i-propyl-pyrazolium perchlorate; | | | | | 4.0 | |
| 1,2-Dimethyl-3,5-diphenyl-4-(2-propynyl)-pyrazolium hydrogen sulfate; | | | | | 5.0 | |
| 3,5-Diphenyl-1,2,4-trimethylpyrazolium methyl sulfate; | | | | | SV | 3.0 |
| 3,5-Diphenyl-1,2,4-trimethylpyrazolium perchlorate | | | | | 5.0 | |

Table II

| Compound | Disease Severity of Plants Sprayed to Run-off with Indicated Rates, ppm | | | | | | | | | | | |
| --- | --- | --- | --- | --- | --- | --- | --- | --- | --- | --- | --- | --- |
| | Cuc. Powdery | | | Wheat Powdery | | | Apple Powdery | | | Barley Powdery | | |
| | 500 | 100 | 50 | 500 | 100 | 50 | 500 | 100 | 50 | 500 | 100 | 50 |
| Untreated Controls | | 5.5 | | | 6.0 | | | 5.9 | | | 5.5 | |
| 4-Benzyl-1,2-dimethyl-3,5-diphenyl-pyrazolium hydrogen sulfate; | 2.0 | 4.0 | 5.0 | 2.0 | 3.3 | 4.3 | 4.7 | 5.5 | 5.5 | 2.0 | | |
| 4-Benzyl-1,2-dimethyl-3,5-diphenyl-pyrazolium perchlorate; | 4.7 | | | 2.0 | 2.0 | 2.8 | | | | 4.0 | 5.0 | |
| 4-(Carboxymethyl)-1,2-dimethyl-3,5-diphenylpyrazolium iodide-, ethyl ester; | | | | 1.5 | 2.0 | 3.0 | | | | | | |
| 1,2-Dimethyl-3,5-diphenyl-4-ethyl-pyrazolium methyl sulfate [and hydrogen sulfate (1:1)]; | SV | 3.0M | 3.5 | 1.3 | 3.0 | 3.3 | 5.0 | 5.5 | | 2.5 | 4.5 | 4.5 |
| 1,2-Dimethyl-3,5-diphenyl-4-n-pentylpyrazolium perchlorate; | 5.0 | 5.0 | | 2.5 | 2.0 | 3.0 | 4.5 | 5.0 | | 3.0 | | |
| 1,2-Dimethyl-3,5-diphenyl-4-n-propylpyrazolium perchlorate; | 4.7 | | | 2.0 | 2.0 | 2.8 | | | | | 4.0 | 5.0 |
| 1,2-Dimethyl-3,5-diphenyl-4-i-propylpyrazolium perchlorate; | 4.0 | | | 2.3 | 4.0 | 5.3 | | 5.5 | 5.5 | 2.0 | 5.0 | |
| 1,2-Dimethyl-3,5-diphenyl-4-(2-propynyl)pyrazolium hydrogen sulfate; | 4.7 | | | 2.0 | 4.0 | 5.0 | 4.7 | 5.5 | | 3.0 | 4.5 | |

Table IIa

| Compound | Disease Severity of Plants Sprayed to Run-off with Indicate Rates, ppm | | | | | | | | | | | |
| --- | --- | --- | --- | --- | --- | --- | --- | --- | --- | --- | --- | --- |
| | Cuc. Powdery | | | Wheat Powdery | | | Apple Powdery | | | Barley Powdery | | |
| | 500 | 100 | 50 | 500 | 100 | 50 | 500 | 100 | 50 | 500 | 100 | 50 |
| Untreated Controls | | 5.5 | | | 5.8 | | | 5.6 | | | 5.1 | |

Table II-continued

| | | | | | | | | | | |
|---|---|---|---|---|---|---|---|---|---|---|
| 3,5-Diphenyl-1,2,4-trimethyl-pyrazolium iodide; | | 2 | | 1.5 | 4.0 | 5.0 | 5M | | 1.0 | 4.0 | 3.0 |
| 3,5-Diphenyl-1,2,4-trimethyl-pyrazolium methyl sulfate; | SV | 4.0 | 5.0 | 1.8 | 3.7 | 4.0 | 4.3M | 5.0 | 2.0 | 4.3 |
| 3,5-Diphenyl-1,2,4-trimethyl-pyrazolium perchlorate; | | | | 1.5 | 5.0 | | | | 2.0 | | |

EXAMPLE 2

Preparation of 2-Sodium-1,3-diphenyl-1,3-propanedione

Dibenzoylmethane (112.3 g, 0.5 mole) is dissolved in anhydrous diethyl ether (2.1). The solution is stirred vigorously and sodium hydride (21.0 g, 0.5 mole) added in portons while maintaining the temperature of the mixture between 7° to 12°C. Upon completion of the addition the reaction mixture is allowed to stir 3 hours. Additional anhydrous ether is added, the solid filtered off, reslurried in anhydrous ether, filtered and dried to give 109.0 g (89%) of the sodium salt of 1,3-diphenyl-1,3-propanedione.

EXAMPLE 3

Preparation of 1,3-Diphenyl-2-n-pentyl-1,3-propanedione n-Pentylbromide (22.6 g, 0.15 mole) is added to an anhydrous solution of 2-sodium-1,3-diphenyl-1,3-propanedione (15.7 g., 0.064 mole) in DMF (150 ml), then the reaction mixture is heated at 80° to 90°C for 5 days. The reaction mixture is cooled, poured into ice water, stirred for 1 hour, and extracted with chloroform (3×75 ml.) Evaporation of the chloroform layer gives an oil which is crystallized from 95% ethanol to give 3.7 g (20%) of product, m.p. 68.5° to 69.5°C.

Analysis calculated for $C_{20}H_{22}O_2$; C, 81.60; H, 7.53. Found: C, 81.50; H, 7.63.

EXAMPLE 4

Preparation of 2-Benzyl-1,3-diphenyl-1,3-propanedione

Benzylbromide (25.5 g, 0.15 mole) is added to a partial solution of 2-sodium-1,3-diphenyl-1,3-propanedione (15.7 g, 0.064 mole) in dry acetone (200 ml). The reaction mixture is stirred at reflux for 39 hours, cooled and poured into ice water (600 ml.). The resulting suspension is filtered, the collected solid is dried and recrystallized from 95% ethanol to give 14.6 g (72%) of product, m.p. 102° to 103°C.

Analysis calculated for $C_{22}H_{18}O_2$: C, 84.25; H, 5.77. Found: C, 83.35; H, 5.89.

EXAMPLE 5

By the procedures of Examples II and III the following additional, 2-substituted, 1,3-diphenyl-1,3-propanediones are prepared:

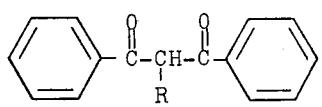

| R | Melting Point °C |
|---|---|
| $CH_3$ | 82–83 |
| $C_2H_5$ | 83–84 |
| n-$C_3H_7$ | 61–62 |
| i-$C_3H_7$ | 81–82 |
| $CH_2$—CH=$CH_2$ | 64–65 |
| $CH_2$—C≡CH | 98–99 |
| $CH_2$—C(=O)—$OC_2H_5$ | 82–83 |
| n-$C_5H_{11}$ | 68.5–69.5 |

EXAMPLE 6

Preparation of 3,5-Diphenyl-4-ethyl-1-methylpyrazole

Methylhydrazine (2.86 g, 0.06 mole) is added to an isopropanol (100 ml) solution of 1,3-diphenyl-2-ethyl-1,3-propanedione (11.0 g, 0.044 mole) with constant stirring at 80°C. The reaction mixture is heated at reflux for 3½ hours, then stirred at room temperature overnight. The reaction mixture is poured into ice water, stirred for ½ hour, and the resulting mixture extracted with chloroform (3×50 ml). Evaporation of the organic layer gives an oil which is crystallized from hexane with cooling to give 6.47 g (56%) or product, m.p. 80° to 81°C.

Analysis calculated for $C_{18}H_{18}N_2$: C, 82.40 H, 6.92: N, 10.68. Found: C, 82.35; H, 7.09; N, 10.75.

EXAMPLE 7

By the process of Example 5 the following additional pyrazoles are prepared:

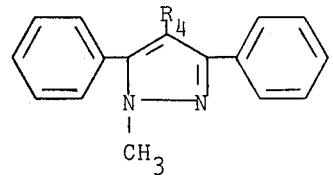

| $R_4$ | Melting Point °C |
|---|---|
| $CH_3$ | 115–116 |
| n-$C_3H_7$ | 74–75 |
| i-$C_3H_7$ | oil |
| $CH_2$—C≡CH | 159–161 |
| $CH_2$—CH=$CH_2$ | 79.5–80.5 |
| n-$C_5H_{11}$ | oil |
| $CH_2$—C(=O)—$OC_2$—$H_5$ | oil |
| $CH_2$—phenyl | 110 |

EXAMPLE 8

Preparation of 3,5-Diphenyl-1,2,4-trimethylpyrazolium methyl sulfate

Dimethylsulfate (7.5 g, 0.06 mole) is added to an anhydrous toluene (100 ml) solution of 1,4-dimethyl-3,5-diphenylpyrazole (10 g. 0.04 mole) at 80°C with stirring. The reaction mixture is stirred at 100°C for 3 hours, cooled and a hygroscopic solid removed by filtration. The solid is dissolved in chloroform and ether is added to the solution gradually. The first fraction which precipitates in extremely hygroscopic, m.p. 94° to 96°C; the second fraction which precipitates in not hygroscopic, m.p. 103° to 105°C as the methyl sulfate; total yield of product 12.6 g (72%).

A 5.0 g portion of the product is dissolved in water, the solution filtered and the filtrate treated with saturated sodium iodide solution. The precipitate is filtered off at 10°C, air dried then redissolved in warm water. The aqueous solution is extracted with ether then with chloroform. The chloroform layer is evaporated, the residual oil triturated with ether to afford 2.8 g (54%) of the iodide salt of the above pyrazolium compound as a white solid, m.p. 196° to 196.5°C.

Similarly, a 3.0 g portion of the pyrazolium methyl sulfate is dissolved in water, the solution filtered and treated with dilute perchloric acid; the precipitate formed is filtered, washed with water and dried to yield 2.5 g (85) of the perchlorate salt of the above pyrazolium compound.

Following the procedure of Example 8, a number of pyrazolium compounds such as listed below are prepared:

1,2-Dimethyl-3,5-diphenyl-4-ethylpyrazolium methyl sulfate, m.p. 115° to 118°C;
1,2-Dimethyl-3,5-diphenyl-4-n-propylpyrazolium perchlorate, m.p. 134° to 135°C;
1,2-Dimethyl-3,5-diphenyl-4-i-propylpyrazolium perchlorate, m.p. 149° to 150°C;
1,2-Dimethyl-3,5-diphenyl-4-n-pentylpyrazolium perchlorate, m.p. 51° to 52.5°C;
1,2-Dimethyl-3,5-diphenyl-4-(2-propynyl)-pyrazolium hydrogen sulfate, m.p. 145° to 151°C;
4-(Carboxymethyl)-1,2-dimethyl-3,5-diphenyl-pyrazolium iodide-, ethyl ester, m.p. 148° to 149°C;
4-Benzyl-1,2-dimethyl-3,5-diphenylpyrazolium hydrogen sulfate, m.p. 244° to 246°C;
4-Benzyl-1,2-dimethyl-3,5-diphenylpyrazolium perchlorate, m.p. 180° to 180.5°C;
4-Allyl-1,2-dimethyl-3,5-diphenylpyrazolium hydrogen sulfate, waxy solid.

We claim:

1. A compound having the formula:

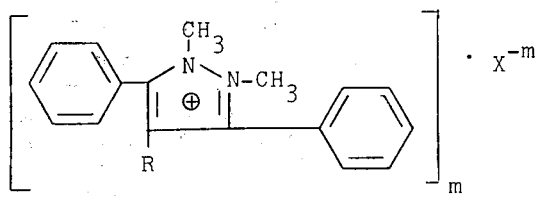

wherein R is a member selected from the group consisting of alkyl $C_2$–$C_5$, allyl, propargyl, benzyl and carbethoxymethyl; X represents an anion having a charge of from 1 to 3; and m represents an integer from 1 to 3.

2. The compound according to claim 1, 4-benzyl-1,2-dimethyl-3,5-diphenylpyrazolium hydrogen sulfate.

3. The compound according to claim 1, 4-(carboxymethyl)-1,2-dimethyl-3,5-diphenylpyrazolium iodide-, ethyl ester.

4. The compound according to claim 1, 1,2-dimethyl-3,5-diphenyl-4-ethylpyrazolium methyl sulfate.

5. The compound according to claim 1, 1,2-dimethyl-3,5-diphenyl-4-n-pentylpyrazolium salt.

6. The compound according to claim 1, 1,2-dimethyl-3,5-diphenyl-4-n-propylpyrazolium salt.

7. The compound according to claim 1, 1,2-dimethyl-3,5-diphenyl-4-i-propylpyrazolium salt.

8. The compound according to claim 1, 4-allyl-1,2-dimethyl-3,5-diphenylpyrazolium salt.

9. The compound according to claim 1, 1,2-dimethyl-3,5-diphenyl-4-(2-propynyl)pyrazolium hydrogen sulfate.

* * * * *